United States Patent [19]

Deetz et al.

[11] Patent Number: 5,231,030

[45] Date of Patent: Jul. 27, 1993

[54] TEMPERATURE INSENSITIVE CALIBRATION SYSTEM

[75] Inventors: David W. Deetz, North Oaks; Russell L. Morris, St. Paul, both of Minn.

[73] Assignee: Diametrics Medical, Inc., Roseville, Minn.

[21] Appl. No.: 837,205

[22] Filed: Feb. 18, 1992

Related U.S. Application Data

[63] Continuation-in-part of Ser. No. 604,666, Oct. 26, 1990, abandoned.

[51] Int. Cl.⁵ .................................... G01N 31/00
[52] U.S. Cl. ................................ 436/8; 436/9; 436/11; 436/16; 436/17
[58] Field of Search .......................... 436/8-18

[56] References Cited

U.S. PATENT DOCUMENTS

| | | | |
|---|---|---|---|
| 4,001,142 | 1/1977 | Turner | 436/11 |
| 4,116,336 | 9/1978 | Sorensen et al. | 436/11 |
| 4,126,575 | 11/1978 | Louderback | 436/11 |
| 4,151,108 | 4/1979 | Sorensen et al. | 436/11 |
| 4,163,734 | 8/1979 | Sorensen et al. | 436/11 |
| 4,279,775 | 7/1981 | Louderback et al. | 436/11 |
| 4,299,728 | 11/1981 | Cormier et al. | 436/11 |
| 4,369,127 | 1/1983 | Cormier et al. | 436/11 |
| 4,469,792 | 9/1984 | Simmonds et al. | 436/11 |
| 4,485,174 | 11/1984 | Chiang et al. | 436/11 |
| 4,722,904 | 2/1988 | Feil | 436/11 |

OTHER PUBLICATIONS

The Merck Index, Martha Windholtz, 1983, p. 549, 10th Edition.

Merck Index, 10th Edition, Windholt et al (eds), p. 3742 (1983).

*Primary Examiner*—James C. Housel
*Assistant Examiner*—Lien Tran
*Attorney, Agent, or Firm*—Haugen and Nikolai

[57] ABSTRACT

A multi-phase control and/or calibration system consists of a liquid phase containing an amount of dissolved oxygen ($O_2$) in which the $O_2$ partial pressure is made relatively temperature insensitive over an ambient temperature range of interest, and an amount of dissolved carbon dioxide ($CO_2$) and one or more solute species that provide temperature stability with respect to the partial pressure of $CO_2$ over the ambient temperature range of interest. The liquid phase is in equilibrium with a vapor phase and the system sealed with a storage atmosphere.

18 Claims, 1 Drawing Sheet

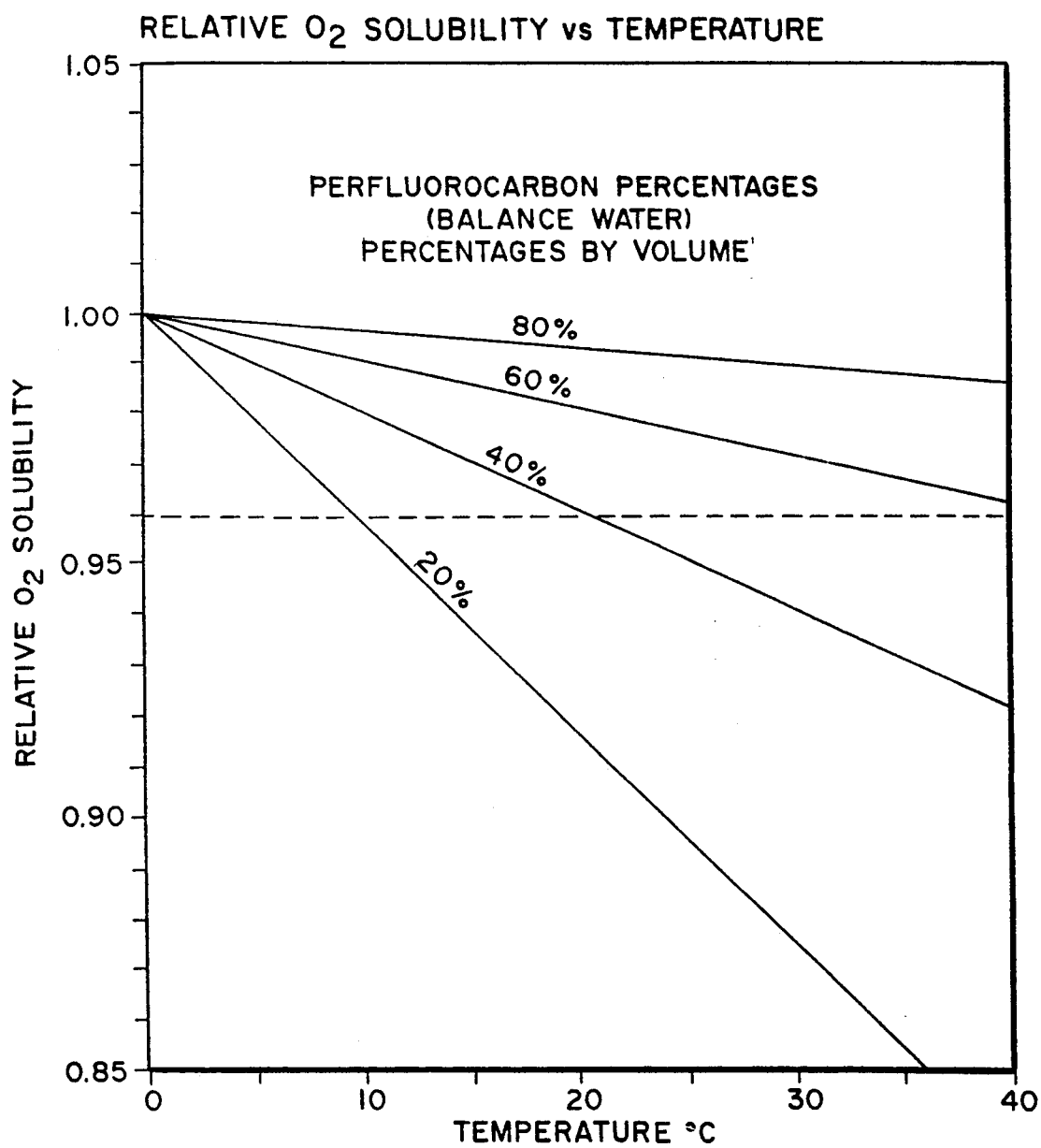

TEMPERATURE INSENSITIVE CALIBRATION SYSTEM

CROSS-REFERENCE TO RELATED APPLICATION

This is a continuation-in-part of application Ser. No. 07/604,666 filed Oct. 26, 1990, now abandoned.

BACKGROUND OF THE INVENTION

1. Field of the Invention

The present invention is directed generally to a multi-phase control or calibration system and, more particularly, to such a system exhibiting relatively constant partial pressures with respect to certain diverse dissolved gaseous species of interest in one or more liquid phases over a range of ambient temperatures. The preferred fluid consists of a first non-aqueous liquid phase containing an amount of dissolved oxygen ($O_2$) in which the partial pressure of $O_2$ is relatively temperature insensitive over an ambient temperature range of interest, a second, aqueous phase, immiscible with the first phase and containing an amount of dissolved carbon dioxide ($CO_2$) and one or more solute species that provide temperature stability with respect to the partial pressure of $CO_2$ over the ambient temperature range of interest. The liquid phases are in equilibrium with a vapor phase.

2. Description of the Related Art

Relatively inert fluids which have the ability to dissolve rather large amounts of oxygen and which are stable and do not affect biological media, for example, are known. The class of fluorinated organic compounds known as perfluorocarbons are the best known examples of such materials. Perfluorocarbon substances are completely fluorinated organic compounds in which all the carbon-bound hydrogen atoms are replaced with fluorine atoms. These materials have an unique combination of properties. The compounds are extremely non-polar and have essentially no solvent action. They are so chemically inert and have such high thermal stability that they can be mixed with almost any material without fear of any adverse reactive effect either upon other mixture components or upon the material itself. The compounds also have a relatively high boiling point and low pour point giving them a relatively wide liquid range. Many of these perfluorocarbon materials also have a high, relatively stable, oxygen solubility.

These properties have led to the use of perfluorocarbon solutions as oxygen carriers and as controls for $O_2$ sensors. Aqueous perfluorocarbon multi-phase emulsions have been proposed for applications which involve the need to carry or sense oxygen in the presence of carbon dioxide and/or where pH needs to be controlled or sensed. These include medical related technologies involving blood and synthetic blood materials and blood gas analysis controls and calibrators. One such emulsion system is illustrated and described in U.S. Pat. No. 4,722,904 to Feil. Other such systems are disclosed in Turner (U.S. Pat. No. 4,001,142), Cormier, et al. (U.S. Pat. Nos. 4,299,728 and 4,369,127) and Sorenson, et al. (U.S. Pat. Nos. 4,116,336 and 4,151,108).

These fluids typically comprise an aqueous emulsion of the organic oxygen carrier. Certain of these emulsions may contain surfactant materials, pH buffers and preservative materials. The aqueous phase and the perfluorocarbon phase are chemically compatible but completely immiscible. While the perfluorocarbon phase reversibly carries the oxygen of interest, the aqueous phase reversibly carries other constituents of interest such as carbon dioxide and hydrogen ions.

The use of such materials, particularly as quality controls for blood gas analyzers, for example, requires that the control system contain a known partial pressure of oxygen and a known partial pressure of carbon dioxide and be of a known pH. Accordingly, the control system must be supplied in gas-tight, sealed ampules, or the like containing known amounts of dissolved oxygen and carbon dioxide species so that equilibrium partial pressures remain constant. Such a known or control substance can later be used to check the relative accuracy of an instrument utilized to measure $O_2$ and $CO_2$ concentration and the pH of such substances as blood.

Although such prior approaches have been successful with respect to achieving proper quality control of such devices, the integrity of the partial pressure of the dissolved species used in control measurements depends on the complete isolation of the control system from the time it is prepared until the time of use. In addition, because of the variation in solubility of the gas species of interest with temperature, the opening and use of the control must occur at a specific temperature; and thus the results are also quite temperature dependent.

There remains a definite need to reduce the sensitivity of such control systems to fluctuating or uncertain ambient temperature conditions. This would lead to more versatile uses of the materials and to the development of accurate device calibration methods without the need for rigorous environmental control at the time of calibration. Accordingly, it is an object of the present invention to develop a calibration/control system which is less temperature sensitive than known fluids of the class including aqueous emulsions of perfluorocarbons.

SUMMARY OF THE INVENTION

In accordance with the present invention, the temperature sensitivity of the partial pressures of dissolved gases of interest has been greatly reduced. The accuracy of calibration system established at a filling temperature of 10° C, for example, will not be sacrificed by later removal at, for example, 30° C.

In the preferred embodiment, the oxygen carrying solution phase is a solution of oxygen in one or more perfluorocarbon materials. The preferred perfluorocarbon materials include FC-43, FC-75, FC-77, and others, manufactured by and available from the 3M Company of St. Paul, Minn. The aqueous solution phase contains a specific amount of $CO_2$ complexing agents such as ethylene diamine, $HCO_3^-$, $Ca^{++}$ and $OH^-$ or other compounds which buffer the partial pressure of carbon dioxide ($CO_2$) in the aqueous solution to changes in temperature. An amount of a compatible pH buffer can also be employed to stabilize the solution with respect to acidity.

The multi-phase control/calibration system of the invention is prepared under tightly controlled conditions and transferred to containers designed to accommodate the desired amount. The filled containers are provided with a sealed storage atmosphere which maintains the desired conditions in equilibrium during the shelf life of the system. This atmosphere typically contains sufficient oxygen and carbon dioxide in a mixture with one or more other gases inert to the system to maintain the desired amount of $O_2$ and $CO_2$ species in the liquid phases of the system.

The preferred range of $O_2$ ($pO_2$) partial pressure with respect to the system is from about 10 to about 200 mm Hg and the preferred range of partial pressure for $CO_2$ ($pCO_2$) is from about 5 to 100 mm Hg. The oxygen solubility stays within accuracy tolerance limits over a range of about 20° C. or greater using the liquid phase system of the invention. The preferred temperature range of temperature relative partial pressure insensitivity is about 10° C. to about 30° C. It is also contemplated that various phase components can be used, if desired, to expand the ambient temperature range of relative partial pressure insensitivity beyond that range to, say, 0° C. to 40° C., if desired. The range 10° to 30° C., however, represents a normal range of temperatures for an indoor conditioned space.

In this regard, it has been found that over the temperature range contemplated, the relative $O_2$ solubility insensitivity can be reduced to less than 1% using an oxygen carrying solution phase containing perfluorocarbon. The preferred co-solvent in this phase is water. The generally accepted tolerance for oxygen calibration error is no more than about four percent (4%) in the range 10° C. to 30° C. This requires a liquid phase containing at least 40% perfluorocarbon by volume and, preferably, at least a 50/50 ratio of perfluorocarbon to water in the case of a perfluorocarbon/water system if desired Increasing the percentage of perfluorocarbon in the liquid phase above the minimum required amount decreases the temperature sensitivity. Accordingly, a solution having 80% perfluorocarbon and 20% water shows less than a 1% change in $O_2$ solubility in the range 10° C. to 30° C. This can be done to decrease the calibration error considerably.

In addition, surfactants or other wetting agents can be added to emulsify the multiliquid phases, if desired. It is also contemplated that the solution of the calibration system of the invention consist of a single aqueous phase containing, in addition to a $CO_2$ binding component or components, one or more solutes which reversibly bind $O_2$, such as copper ions, hemoglobin, and transition metal macromolecular complexing agents. These include mesotetraphenyl porphorin complexes of Co(II), Co(III), Mn(III) and Fe(II).

Solutions formulated in accordance with the invention should exhibit stable overall solubilities of the gases of interest over a 20° C. or greater range of ambient temperatures. This means that calibration/control systems in impermeable containers which are filled under strictly controlled conditions at one temperature may be removed from a storage atmosphere at a different temperature and used with complete confidence.

BRIEF DESCRIPTION OF THE DRAWING

The single FIGURE shows the theoretical relative solubility of oxygen ($O_2$) in various combinations of the perfluorocarbon (FC-43) with water as a liquid phase in a linear mixing model.

DETAILED DESCRIPTION

Although there are some exceptions, notably dilute solutions of hydrogen chloride in water, the solubility of most gases in liquids decreases with increases in temperature. It is further well known that the equilibrium solubility of any volatile constituent of a solution at a given temperature is related to the partial pressure of that constituent in the vapor phase above the liquid at any given temperature. It follows, then, that solutions of critical concentrations of dissolved gaseous species and liquids have an extreme sensitivity both to changes in the partial pressure of each such species above the solution and to changes in temperature of the solution. Prior to the present invention, it has heretofore been necessary to expose the calibration/control system to the ambient environment only at a specific temperature to preserve the compositional integrity of the system.

This has heretofore always been the case with respect to control solutions, including those in which oxygen is carried by a perfluorocarbon in one phase and carbon dioxide is carried in a second aqueous solution phase of controlled pH which are used to calibrate biological sensors utilized to detect dissolved oxygen, carbon dioxide and acidity. Because of the inherent properties of these systems, it has always been assumed that the temperature limitation with respect to exposure was one which had to be accommodated and could not be overcome.

According to the present invention, however, it has been discovered that such multi-phase solutions can, indeed, be made less sensitive to variations in ambient temperature over the range of ambient temperatures normally encountered in indoor conditioned spaces, e.g., 10° C. to 30° C., or beyond. This is further illustrated in the plots of the FIGURE where it can be seen that a liquid phase of 80% (vol) of the perfluorocarbon FC-43 in water exhibits an oxygen solubility loss of only about 1% from 0° C. to 40° C. Other perfluorocarbons show similar results. The higher the percentage composition of perfluorocarbon, the more stable the solubility. For accuracies in $O_2$ measurement $\leq$ about 4% (0.2%/° C.) over a 20° C. span, a concentration of perfluorocarbon $>40\%$ is required. The dashed reference line in the FIGURE represents a 4% loss in solubilized $O_2$ (from 100% to 96%). At least that much loss will occur with a 40% solution over a 20° C. span. For most applications, this represents more of a deviation than is generally tolerable, however; and accordingly, a solution having a concentration of perfluorocarbon of at least 50% is preferable and, as shown in the FIG. at least 60% yields results within the tolerance for $O_2$ solubility (4% loss) over the entire range of 0°–40° C. The stability of the solubility can be tailored to the needs of the particular application with respect to expected exposure temperature range and required accuracy of instrument calibration. It is expected that for some applications a rather high $\geq 80\%$ concentration of perfluorocarbon may be required.

It should further be noted that the reduction of temperature sensitivity with respect to oxygen in a perfluorocarbon/water phase is the most important aspect of its application in the invention. Whether the viscosity of the solution is raised, or whether the actual amount of oxygen in solution increases with increased perfluorocarbon concentration clearly have little application.

While it has been found that a variety of perfluorocarbon substances exhibit rather stable properties with respect to dissolving amounts of oxygen in the range of 10° C.–30° C. and, in some instances, even beyond this range, the same cannot be said of the relative concentration of dissolved $CO_2$, which decreases with increasing temperature. In accordance with the invention, it has further been discovered, however, that the use of a dissolved species, such as ethylene diamine in the aqueous phase of the multi-phase calibration solution, can stabilize the amount of carbon dioxide dissolved in the aqueous solution. In fact, the overall partial pressure of $CO_2$ can be substantially linearized over a temperature range comparable to that of $O_2$ in the perfluorocarbon. Compatible buffers can also be added to the aqueous solution to control acidity at the desired pH value.

The solutions or liquid phases in accordance with the invention are prepared under controlled conditions. Known amounts of the dissolved gases $O_2$ and $CO_2$ are present in the phases as prepared. However, it may be months or even years before the system is actually used so that long-term stability is required. To preserve the integrity of the system over the shelf life of the product, the calibration system is sealed in an impermeable fluid tight container together with an amount of storage atmosphere which contains sufficient $pO_2$ and $pCO_2$ to maintain the amount of dissolved species in the liquids over time.

The container may be a glass ampule, or the like, but is preferably a polymeric envelope or laminated pouch which may consist of several layers of metallic foil and polymeric materials which make the pouch impervious to atmosphere exchange with the environment.

When the seal of the encapsulating container is breached, of course, the protective or storage atmosphere is lost. The calibration system of the present invention, however, maintains its known $pO_2$, $pCO_2$ and pH for the relatively shorter time required to perform the control or calibration procedure, regardless of the ambient temperature at which the breach occurs as long as that temperature is in the range of relative stability for the system, e.g., 10° C.-30° C.

It is apparent that the calibration system of the present invention can also function well as a control system for analytical instruments of the class normally employing such controls as periodic checks. Controls generally require somewhat less precision than calibration systems.

This invention has been described in this application in considerable detail in order to comply with the Patent Statutes and to provide those skilled in the art with the information needed to apply the novel principles and to construct and use such specialized components as are required. However, it is to be further understood that the invention can be carried out by specifically different equipment and devices and that various modifications can be accomplished without departing from the scope of the invention itself.

What is claimed is:

1. A liquid calibration system medium which has a capacity for dissolving $O_2$ in which the relative solubility of $O_2$ in the medium remains within desired limits over a given temperature range and wherein the calibration medium comprises at least 50% by volume of a perfluorocarbon material and wherein the balance of the medium consists essentially of water.

2. The liquid calibration system medium of claim 1 wherein the given temperature range is from about 0° C. to about 40° C.

3. The liquid calibration system medium of claim 1 characterized by a rate of change in the relative solubility of $O_2$ with temperature is $\leq 0.2\%$ per ° C.

4. The liquid calibration system medium of claim 2 characterized by a rate of change in the relative solubility of $O_2$ with temperature is $\leq 0.2\%$ per ° C.

5. The liquid calibration system medium of claim 1 wherein the medium contains 80% or more of perfluorocarbon.

6. The liquid calibration system medium of claim 1 characterized by a rate of change in the relative solubility of $O_2$ with temperature is $\leq 0.05\%$ per ° C.

7. The liquid calibration system medium of claim 6 wherein the given temperature range is from bout 0° C. to about 40° C.

8. The liquid calibration system medium of claim 5 characterized by a rate of change in the relative solubility of $O_2$ with temperature is $\leq 0.05\%$ per ° C.

9. The liquid calibration system medium of claim 8 wherein the given temperature range is from about 0° C. to about 40° C.

10. A calibration system which is relatively temperature insensitive over an ambient temperature range of interest, comprising:

a liquid phase comprising at least 50 percent by volume of a perfluorocarbon with the balance being essentially water, an amount of $O_2$ dissolved therein, a solute having a capacity for reversibly reacting with carbon dioxide ($CO_2$) and an amount of $CO_2$ reversibly reacted therewith;

a vapor phase in contact with the liquid phase, the system being insensitive to changes in the relative volume occupied by the vapor phase in relation to that occupied by the liquid phase;

a fluid tight enclosure for containing the calibration system including the vapor phase; and wherein the partial pressure of both $O_2$ and $CO_2$ remains substantially constant within predetermined tolerances over the ambient temperature range of interest.

11. The calibration system of claim 10 wherein an aqueous portion of the liquid phase contains at least one solute species selected form the group consisting of ethylenediamine and $OH^-$ ions.

12. The temperature insensitive calibration system of claim 10 wherein the liquid phase consists of at least 60% by volume perfluorocarbon material.

13. The calibration system of claim 10 wherein the partial pressure of $O_2$ is in the range of about 10 to 200 mm Hg and wherein the partial pressure of $CO_2$ is in the range of about 5 to 100 mm Hg.

14. A calibration system having a liquid calibrant in contact with a vapor phase characterized by a relatively temperature independent equilibrium characteristic with respect to the partial pressure of gaseous species of interest in a liquid phase over an ambient temperature range of form approximately 0° C. to 40° C. comprising:

the liquid calibrant comprising an amount of $O_2$ dissolved in a liquid perfluorocarbon phase, wherein the liquid perfluorocarbon phase is at least 50% by volume of the liquid calibrant and wherein the balance consists essentially of an aqueous phase containing an amount of at least one solute which reversibly reacts with $CO_2$ such that the partial pressure of $O_2$ and $CO_2$ change within known limits with respect to changes in temperature in the ambient temperature range; and a fluid tight container for storing the calibration system;

a vapor phase in equilibrium with the liquid calibrant including an amount of storage atmosphere of known composition hermetically sealed in the fluid tight container with the calibration system;

the system being insensitive to changes in the relative amount of the vapor phase in relation to the liquid calibrant.

15. The calibration system of claim 14 wherein the ambient temperature range is from 10° C. to 30° C.

16. The calibration fluid of claim 15 wherein the aqueous liquid phase further contains an amount of at least one buffer to control the ph and wherein the aqueous phase contains at least one solute species selected from the group consisting of ethylediamine and $OH^-$ ions.

17. The calibration system of claim 15 wherein the partial pressure of $O_2$ is in the range of about 10 to 200 mm Hg and wherein the partial pressure of $CO_2$ is in the range of about 5 to 100 mm Hg.

18. The calibration system of claim 14 wherein the liquid perfluorocarbon is at least 60% by volume of the liquid calibrant.

* * * * *

UNITED STATES PATENT AND TRADEMARK OFFICE
CERTIFICATE OF CORRECTION

PATENT NO. : 5 231 030
DATED : July 27, 1993
INVENTOR(S) : David W. Deetz et al

It is certified that error appears in the above-identified patent and that said Letters Patent is hereby corrected as shown below:

In column 6, line 5, delete "bout" and insert -- about -- .

In column 6, line 49, delete "form" and insert -- from -- .

In column 7, line 5, delete "ph" and insert -- pH -- .

Signed and Sealed this

Fifteenth Day of March, 1994

Attest:

BRUCE LEHMAN

Attesting Officer

Commissioner of Patents and Trademarks